(12) United States Patent
Kyvik et al.

(10) Patent No.: US 10,350,388 B2
(45) Date of Patent: Jul. 16, 2019

(54) PERIPHERAL INTRAVENOUS AND ARTERIAL CATHETER SECUREMENT DEVICE

(71) Applicant: TIDI Securement Products, LLC, Neenah, WI (US)

(72) Inventors: Kurt T. Kyvik, Satellite Beach, FL (US); Arthur Parkhurst, Ocala, FL (US)

(73) Assignee: TIDI Securement Products, LLC, Neenah, WI (US)

( * ) Notice: Subject to any disclaimer, the term of this patent is extended or adjusted under 35 U.S.C. 154(b) by 693 days.

(21) Appl. No.: 14/873,923

(22) Filed: Oct. 2, 2015

(65) Prior Publication Data

US 2016/0067451 A1     Mar. 10, 2016

Related U.S. Application Data

(63) Continuation-in-part of application No. 29/501,593, filed on Sep. 5, 2014, now Pat. No. Des. 780,914.

(51) Int. Cl.
*A61M 25/02*     (2006.01)

(52) U.S. Cl.
CPC ..... *A61M 25/02* (2013.01); *A61M 2025/0246* (2013.01); *A61M 2025/0253* (2013.01); *A61M 2025/0266* (2013.01); *A61M 2025/0273* (2013.01)

(58) Field of Classification Search
CPC .. A61M 2025/0273; A61M 2025/0266; A61M 25/02; A61F 13/0203; A61F 13/024; A61F 13/105
See application file for complete search history.

(56) References Cited

U.S. PATENT DOCUMENTS

| | | | |
|---|---|---|---|
| 2,875,758 A * | 3/1959 | Fuzak | A61F 13/105 602/58 |
| 3,138,158 A | 6/1964 | Gordon et al. | |
| 3,167,072 A | 1/1965 | Stone et al. | |
| 3,826,254 A | 7/1974 | Mellor | |
| 3,834,380 A | 9/1974 | Boyd | |
| 3,918,446 A | 11/1975 | Buttaravoli | |
| 3,973,565 A | 8/1976 | Steer | |
| 4,129,128 A | 12/1978 | McFarlane | |
| 4,250,880 A | 2/1981 | Gordon | |

(Continued)

FOREIGN PATENT DOCUMENTS

| | | |
|---|---|---|
| CN | 203123273 | 8/2013 |
| DE | 20020326 U1 | 2/2001 |

(Continued)

*Primary Examiner* — Nathan R Price
*Assistant Examiner* — Justin L Zamory
(74) *Attorney, Agent, or Firm* — Boyle Fredrickson, S.C.

(57) ABSTRACT

A catheter securement bandage may include a base layer formed with a multi-ply laminate comprising adhesive, gauze, and plastic layers. A top layer may similarly be formed with a multi-ply laminate comprising a layer adhesive, plastic, gauze, and an added layer of adhesive. By securing a hub portion and lure connector of a catheter, the catheter securement bandage maintains an optimal catheter insertion angle of the catheter into a patent this preventing kinking and obstruction of flow through the catheter.

6 Claims, 3 Drawing Sheets

(56) References Cited

U.S. PATENT DOCUMENTS

| | | | |
|---|---|---|---|
| 4,324,237 A * | 4/1982 | Buttaravoli | A61M 25/02 602/54 |
| 4,460,356 A | 7/1984 | Moseley | |
| 4,490,141 A | 12/1984 | Lacko et al. | |
| 4,519,793 A | 5/1985 | Galindo | |
| 4,699,616 A | 10/1987 | Nowak et al. | |
| 4,717,385 A | 1/1988 | Cameron et al. | |
| 4,767,411 A | 8/1988 | Edmunds | |
| 4,822,342 A | 4/1989 | Brawner | |
| 4,832,009 A * | 5/1989 | Dillon | A61F 13/0203 424/447 |
| 4,838,868 A | 6/1989 | Forgar et al. | |
| 4,863,432 A | 9/1989 | Kvalo | |
| 4,874,380 A | 10/1989 | Hesketh | |
| 4,915,694 A | 4/1990 | Yamamoto et al. | |
| 5,037,397 A | 8/1991 | Kalk et al. | |
| 5,192,274 A | 3/1993 | Bierman | |
| 5,215,532 A | 6/1993 | Atkinson | |
| 5,219,336 A | 6/1993 | Wilk | |
| 5,224,935 A | 7/1993 | Hollands | |
| 5,232,453 A | 8/1993 | Plass et al. | |
| 5,236,421 A | 8/1993 | Becher | |
| 5,282,791 A | 2/1994 | Lipton et al. | |
| 5,370,627 A | 12/1994 | Conway | |
| 5,380,294 A | 1/1995 | Persson | |
| 5,413,562 A | 5/1995 | Swauger | |
| 5,685,859 A | 11/1997 | Kornerup | |
| 6,273,873 B1 | 8/2001 | Fleischer | |
| 6,419,660 B1 | 7/2002 | Russo | |
| 6,428,516 B1 | 8/2002 | Bierman | |
| D470,936 S | 2/2003 | Bierman | |
| 6,689,104 B2 | 2/2004 | Bierman | |
| D492,411 S | 6/2004 | Bierman | |
| 6,765,122 B1 | 7/2004 | Stout | |
| 6,770,055 B2 | 8/2004 | Bierman et al. | |
| 6,827,706 B2 | 12/2004 | Tollini | |
| 6,837,875 B1 | 1/2005 | Bierman | |
| 6,866,652 B2 | 3/2005 | Bierman | |
| D503,977 S | 4/2005 | Bierman | |
| 6,875,200 B1 | 4/2005 | Ajagbe | |
| 6,929,625 B2 | 8/2005 | Bierman | |
| 6,951,550 B2 | 10/2005 | Bierman | |
| 6,979,320 B2 | 12/2005 | Bierman | |
| 7,018,362 B2 | 3/2006 | Bierman et al. | |
| D528,206 S | 9/2006 | Bierman | |
| 7,137,968 B1 | 11/2006 | Burrell et al. | |
| 7,524,307 B2 | 4/2009 | Davis et al. | |
| 7,637,894 B2 | 12/2009 | Fleisher | |
| D608,444 S | 1/2010 | Kyvik et al. | |
| D608,887 S | 1/2010 | Kyvik et al. | |
| 7,648,485 B2 | 1/2010 | Fleisher | |
| D616,091 S | 5/2010 | Kyvik et al. | |
| D616,542 S | 5/2010 | Kyvik et al. | |
| D616,983 S | 6/2010 | Kyvik et al. | |
| 7,766,880 B1 | 8/2010 | Spinoza | |
| D625,002 S | 10/2010 | Kyvik et al. | |
| 7,812,212 B2 | 10/2010 | Propp et al. | |
| D652,509 S | 1/2012 | Kyvik et al. | |
| 8,128,602 B2 | 3/2012 | Tollini et al. | |
| 8,157,770 B2 | 4/2012 | Elwell et al. | |
| D663,834 S | 7/2012 | Kyvik et al. | |
| 8,241,253 B2 | 8/2012 | Bracken | |
| 8,251,957 B2 | 8/2012 | Kyvik et al. | |
| 8,500,698 B2 | 8/2013 | Kyvik et al. | |
| 8,608,706 B2 | 12/2013 | Davis et al. | |
| 8,834,427 B2 | 9/2014 | Kyvik et al. | |
| D715,927 S | 10/2014 | Kyvik et al. | |
| D715,928 S | 10/2014 | Kyvik et al. | |
| 2002/0195114 A1 | 12/2002 | Tollini | |
| 2010/0298778 A1 | 11/2010 | Bracken | |
| 2011/0021997 A1 | 1/2011 | Kyvik et al. | |
| 2012/0316504 A1 | 12/2012 | Kyvik et al. | |
| 2013/0096507 A1 | 4/2013 | Lelievre | |
| 2013/0150796 A1 | 6/2013 | Souza et al. | |

FOREIGN PATENT DOCUMENTS

| | | |
|---|---|---|
| EP | 0408389 | 1/1991 |
| GB | 2464662 A | 4/2010 |
| KR | 20-2008-0004611 | 10/2008 |
| KR | 10-2010-0114171 | 10/2010 |

* cited by examiner

PERIPHERAL INTRAVENOUS AND ARTERIAL CATHETER SECUREMENT DEVICE

CROSS REFERENCE TO OTHER APPLICATIONS

This application claims priority and is a continuation in part of U.S. Ser. No. 29/501,593 filed on Sep. 5, 2014, the entire contents of which are hereby expressly incorporated by reference into the present application.

BACKGROUND OF THE INVENTION

1. Field of the Invention

This invention is related to the field of peripheral intra-venous and arterial catheter securement, including catheters with suture wings and ports.

2. Discussion of the Related Art

Peripheral intra-venous and arterial catheters traditionally have been secured to the skin by using tape, transparent dressings and sutures. In a medical facility, technique for securement with tape is inconsistent, can be harsh on skin and often does not properly remain secure. The addition of a transparent dressing adds somewhat to security depending on application technique. Typical transparent dressing applications provide gaps down the side of the catheter and extension set. Additionally, tape and transparent dressing applications are designed to press the catheter and extension set connectors down onto the skin raising the potential for skin irritation. Securing catheters with sutures contributes to complications through infection of additional puncture wounds in the skin and raises the potential for accidental needle stick injury to the clinician. An additional problem with known catheter securement is that the angle of entry of the catheter into a patient commonly causes a bending of the catheter. This bending can cause a kink and obstructs or minimizes flow through the catheter.

Additionally, catheters are commonly picked and pulled at whether unintentionally or intentionally by a patient. Loosely attached catheters can be pulled out of the patient by getting caught on an object or through "twiddle syndrome" which arises when a fidgety patient subconsciously picks and pulls at the catheter and or dressing.

What is therefore needed is a catheter securement that maintains a catheter at the optimal entry angle, attaches to a patient without the use of sutures, staples, or any other penetrating device, protects the skin from irritation, and prevents any dirt or debris from getting under the catheter.

SUMMARY AND OBJECTS OF THE INVENTION

A catheter securement bandage may include a base layer formed with a multi-ply laminate with a first layer of adhesive, a second layer of gauze, and a third layer of plastic. A top layer may also be formed with a multi-ply laminate comprising a first layer of adhesive, a second layer of plastic, a third layer of gauze, and a fourth layer of adhesive wherein the first layer of adhesive on the top layer secures to the third layer of plastic on the base layer.

The top layer may include a first adhesive tab configured to attach to a hub portion of a catheter with an adhesive and a second adhesive tab configured to attach to a lure connector with an adhesive.

A first release liner may be provided to protect at least a portion of the adhesive on the base layer. Similarly, a second release liner may be provided to protect at least an additional portion of the adhesive on the base layer. The first release liner and the second release liner may also have a length longer than a length of the base layer to allow a nurse to wrap the first and second adhesive tabs around a lure connector and hub portion with sufficient length available to secure to the base layer.

The first release liner and the second release liner may only partially contact the first layer of adhesive on the base layer. This allows the medical care giver to peel the protection and apply each part to a patient's skin, one at a time.

The first release liner and the second release liner may each comprise a first length in contact with the first layer of adhesive on the base layer and a free-floating end not in contact with the first layer of adhesive on the base layer, thus producing a fold.

A perforation along a central portion of the top layer may effectively equally divide at least a portion of the top layer into the first adhesive tab and the second adhesive tab. The top layer may also have a free-floating end, prior to attachment to a patient, and a distal second end attached to a central portion of the third layer of plastic on the base layer. The perforation may also extend only along the free-floating end of the top layer.

A method of securing a catheter with a catheter securement bandage is also herein disclosed. The method may include removing a first release liner protecting at least a portion of an adhesive on a base layer formed with a multi-ply laminate comprising a first layer of adhesive, a second layer of gauze, and a third layer of plastic. Affixing the portion of the first layer of adhesive to a patient secures it in place. The method also includes removing a second release liner protecting at least an additional portion of the adhesive on the base layer and affixing the additional portion of the first layer of adhesive to the patient. Following that, the method includes removing a third release liner protecting an adhesive on a top layer formed with a multi-ply laminate comprising a first layer of adhesive, a second layer of plastic, a third layer of gauze, and a fourth layer of adhesive, wherein the first layer of adhesive at least partially secures to the third layer of plastic of the base layer.

The method follows with dividing the top layer into two adhesive tabs comprising a first adhesive tab and a second adhesive tab and wrapping the adhesive on the first adhesive tab around a hub portion of a catheter with an adhesive. Subsequently, the method includes securing the adhesive on the first adhesive tab to the third layer of plastic on the base layer, wrapping the adhesive on the second adhesive tab around a lure connector of an IV, and securing the adhesive on the second adhesive tab to the third layer of plastic on the base layer.

To prevent kinking of the catheter, the method includes forming an inclined angle between a central axis of the hub portion of the catheter and a skin surface of the patient at an entry point of the catheter and maintaining the inclined angle with the first and second adhesive tab. An adhesive on a central portion of the base layer assists in keeping the catheter at the proper insertion angle.

These and other aspects and objects of the present invention will be better appreciated and understood when considered in conjunction with the following description and the accompanying drawings. It should be understood, however, that the following description, while indicating preferred embodiments of the present invention, is given by way of illustration and not of limitation. Many changes and modifications may be made within the scope of the present invention without departing from the spirit thereof, and the invention includes all such modifications.

BRIEF DESCRIPTION OF THE DRAWINGS

A clear conception of the advantages and features constituting the present invention, and of the construction and operation of typical mechanisms provided with the present invention, will become more readily apparent by referring to the exemplary, and therefore non-limiting, embodiments illustrated in the drawings accompanying and forming a part of this specification, wherein like reference numerals designate the same elements in the several views, and in which.

Figure 1:
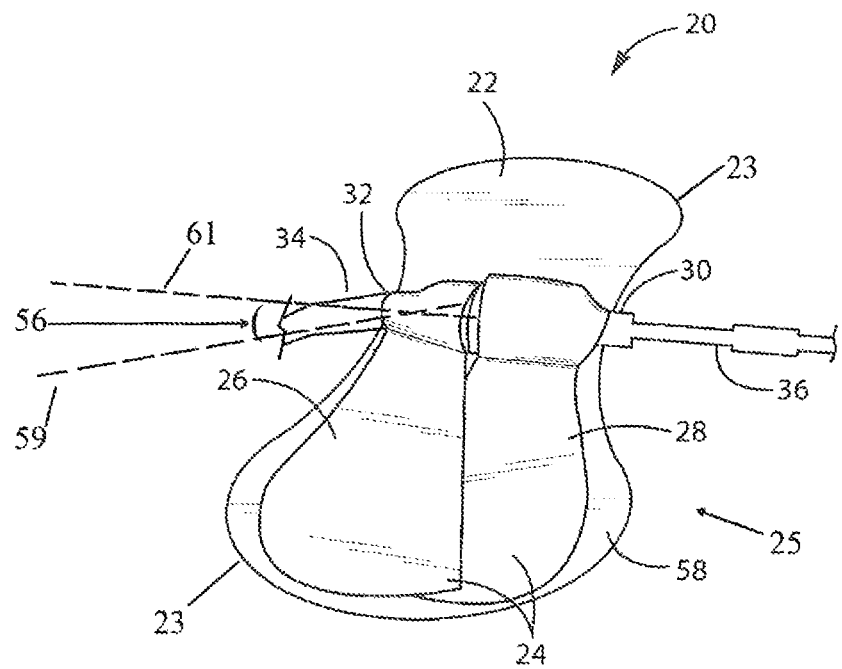
FIG. 1 is a perspective view of a catheter adhesive device attached to a patient and fully securing a catheter and luer connector extension set.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the words connected, attached, or terms similar thereto are often used. They are not limited to direct connection but include connection through other elements where such connection is recognized as being equivalent by those skilled in the art.

DETAILED DESCRIPTION OF EMBODIMENTS

The present invention and the various features and advantageous details thereof are explained more fully with reference to the non-limiting embodiments described in detail in the following description.

1. System Overview

The inventive catheter securement, bandage is a catheter stabilization device that is strong enough to lock intravenous, "IV", and arterial catheters securely in place, yet versatile enough for almost every patient. According to published studies, there is up to 92% failure rate for patients receiving peripheral IV therapy. Common standards of practice and the US Centers for Disease Controls recommend the use of manufactured securement devices. Effective catheter stabilizing has been shown to reduce IV access complications by preventing catheter positioning. When compared to tape, securement devices can reduce complications by as much as 67%, reduce unscheduled restarts from 71% to 17%, and reduce phlebitis by as much as 80%.

The inventive catheter securement bandage secures the catheter and hub portion from the top, bottom and sides. The unique wrap-around design provides securement that maintains optimal catheter insertion angle and provides protection for the skin from hard plastic parts. The catheter securement bandage works with non-winged IV catheters and many winged catheter designs, and makes it easy to standardize clinician securement application.

The invention works universally with all luer connectors and needle-free access devices and is so flexible it can secure even difficult locations on adult fingers. The catheter securement bandage features soft and flexible design with no hard plastic parts for improved patient comfort. The luer connector can be removed or changed while the catheter remains secured. The catheter securement bandage provides superior securement for both horizontal and vertical lifting accidental line pulls. The catheter securement bandage is preferably hypoallergenic, breathable and latex-free to reduce the risk of allergic reactions and skin irritation. By securing both the catheter, hub portion, and luer connector the catheter securement bandage maintains optimal catheter insertion angle.

2. Detailed Description of Embodiments

Figure 2:
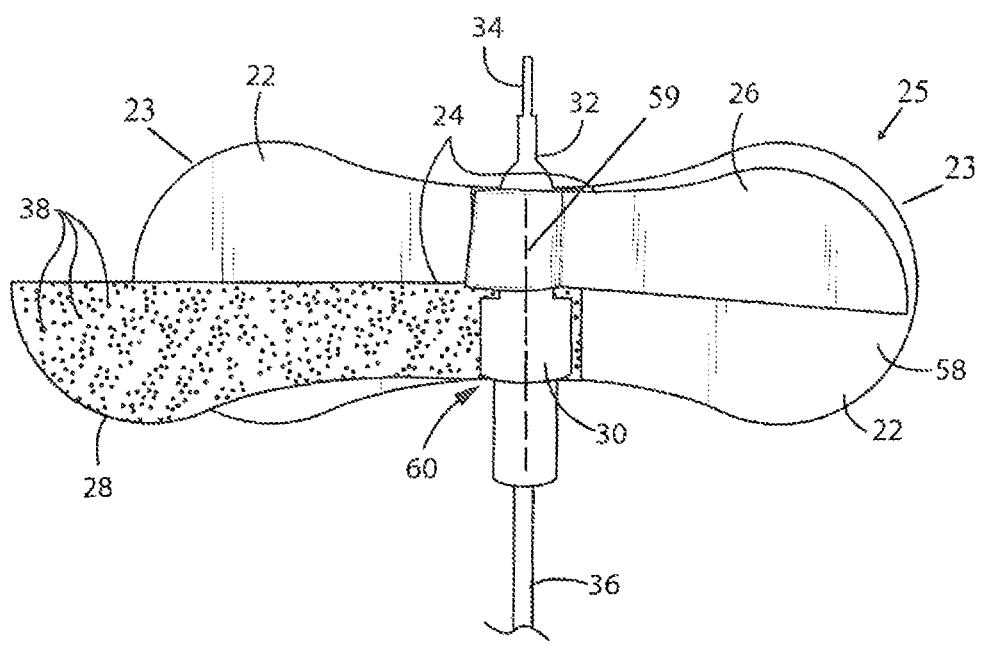
FIG. 2 is a top elevation view of the catheter adhesive device according to FIG. 1 with an adhesive tab removed from the luer connector extension set, exposing adhesive, and a portion of the catheter adhesive device partially securing a catheter.

Referring to FIGS. 1 and 2, the top side of the catheter securement bandage 20 is shown. The catheter securement bandage 20 is formed by joining together a base layer 22 to a top layer 24. The base layer 22 may be formed in any shape with any size and dimensions. Preferably, the base layer 22 is formed by two circular shapes 23 joined together symmetrically making a "figure eight" 25 outline. The top layer 24 is similarly shaped as the base layer 22, without one of the circular shapes. The top layer 24 is also attached to the base layer 22 offset from the central portion 60 of the base layer 22.

The catheter securement bandage 20 is designed to retain a catheter 34 and hub portion 32 of a lure connector 30 securely in place at a proper insertion angle. In order to maintain a proper insertion angle, a first adhesive tab 26 may be wrapped around the hub portion 32 and secured onto the base layer 22. The second adhesive tab 28 may similarly retain the lure connector 30 in place at the proper angle by wrapping around the lure connector 30. The first adhesive tab 26 and the second adhesive tab 28 form the top layer 24.

Figure 5:
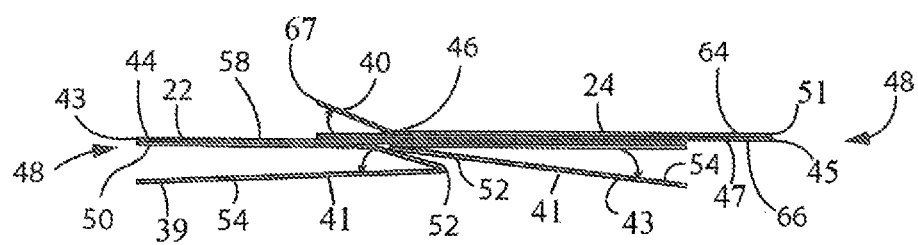
FIG. 5 is a side view of the catheter adhesive device according to FIG. 1 with all release liner in place.

Both the top layer 24 and the base layer 22 are constructed using a multi-ply laminate 48 best shown in FIG. 5. The multi-ply laminate 48 is made of multiple layers that are held together with adhesive 38. The adhesive 38 is preferably a tacky substance in the form of a gel, paste, liquid, or semi-solid so as to allow it to be sufficiently malleable to conform to the curvature of human skin and be flexible along with the catheter securement bandage 20. Known devices such as hook and loop have shown to be undesirable as the hook portion will only secure to a loop portion. An adhesive 38, however; can stick to any surface, even itself. In order to prevent the adhesive 38 from sticking to an object, a thin, stretchable, deformable plastic layer, referred to as a release liner, may be applied. This allows the adhesive 38 to stick to a patient's skin on one side, and not stick to other objects such as clothing or blankets on the opposing side.

Another layer forming the catheter securement bandage 20 is preferably a gauze material. The gauze material is preferably a woven cotton material but may be any known, absorbable, and sterile cloth. The gauze material may be impregnated with the adhesive or may be coated with the adhesive. When applied to the patient, the gauze serves multiple purposes. Gauze works as an absorbent quickly absorbing any fluids and also provides strength to the stretchable plastic. The strength provided by the gauze prevents the plastic from over-stretching when pulled and also provides structural rigidity to the catheter securement bandage 20 making it easier to apply and handle.

Figure 3:
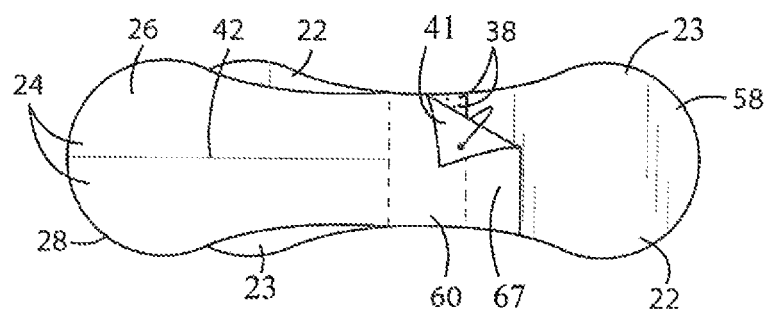
FIG. 3 is a bottom elevation view of the catheter adhesive device according to FIG. 1 with an release liner partially removed from the bottom of the catheter adhesive device.
Figure 6:
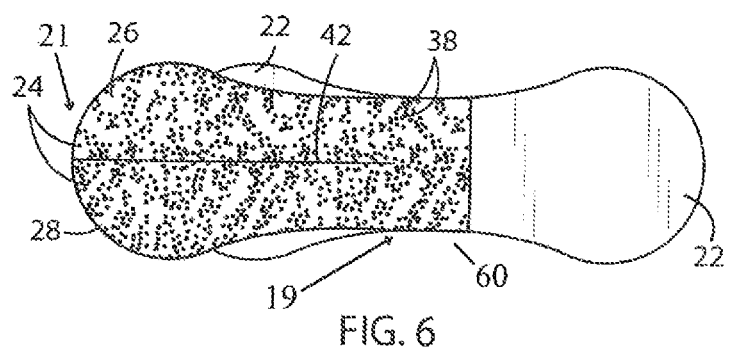
FIG. 6 is a top elevation view of the catheter adhesive device according to FIG. 1 with the release liner fully removed from the adhesive tabs.

Referring to FIGS. 3 and 6, the top layer 24 is shown with the release liner 67 attached. Preferably, the release liner 67 on the top layer 24 is a single, solid piece and does not include a perforation 42. Alternatively, the perforation 42 may be made on the first and second adhesive tabs, 26, 28 as well as the release liner 67 covering said tabs. Adhesive 38 may also be used on the top surface 58 of the base layer 22 in a central portion 60 of the base layer 22. The adhesive 38 on the top surface 58 provides added securement of the lure connector 30 and hub portion 32 when they are in place as is shown in FIGS. 1 and 2, for example. Each one of the first adhesive tab 26 and the second adhesive tab 28 include a free-floating end 21 and a distal second end 19 attached to a central portion 60 of the base layer 22.

Referring specifically to FIG. 5, the multiple layers of the multi-ply laminate 48 may be seen. The base layer 22 includes a first release liner 39 and a second release liner 43 which cover a first layer of adhesive 50 on the bottom side 66 of the base layer 22. The first layer of adhesive 50 may be applied as a coating to the second layer of gauze 45 or it may be impregnated into the gauze. A third layer of plastic 44 covers the entire top surface 58 of the base layer 22 including the portion underneath the top layer 24.

The first release liner 39 and second release liner 43 on the base layer 22 form two separate parts that are each folded, forming folds 52, on opposing sides of the base layer 22. The folds 52 allow medical personnel, such as a nurse, to remove the first release liner 39 on the base layer 22 by grabbing the unattached portion 54 and peeling back the first release liner 39 thus exposing the first layer of adhesive 50 on the base layer 22. The exposed first layer of adhesive 50 may then be securely affixed to a patient's skin. At this point, the medical care giver may grab the opposing unattached portion 54 of the second release liner 43 on the base layer 22 and pull off the unattached portion 54 to stretch the base layer 22 and expose the first layer of adhesive 50 at the same time. The medical care giver may also affix the exposed first layer of adhesive 50 on the base layer 22 at that time thus fully attaching the catheter securement bandage 20 to the patient's skin.

Figure 4:
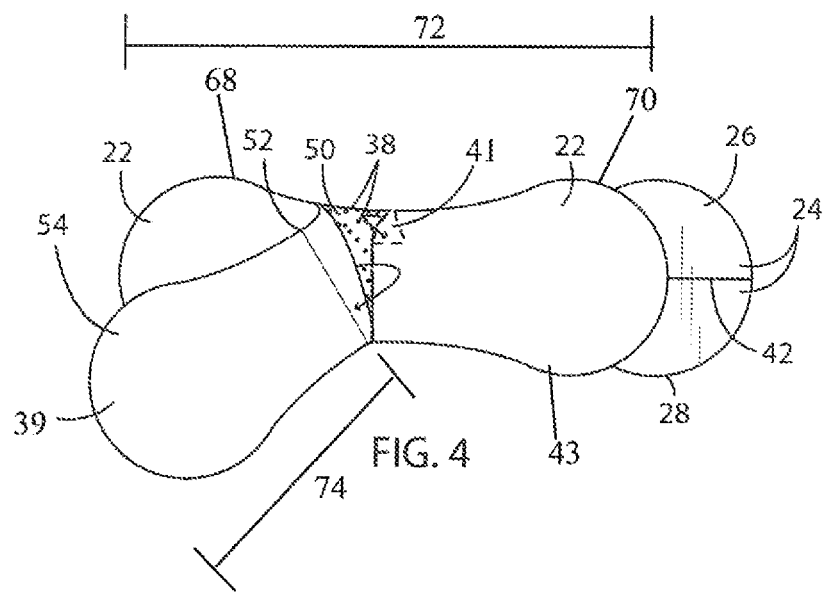
FIG. 4 is a bottom elevation view of the catheter adhesive device according to FIG. 1 with release liner partially removed from adhesive on the bottom of the catheter adhesive device.
Figure 7:
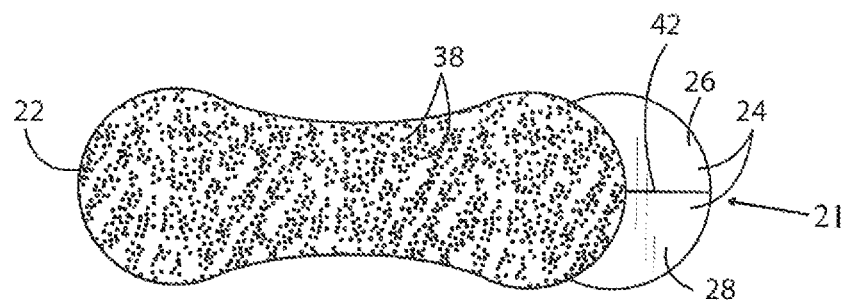
FIG. 7 is a bottom elevation view of the catheter adhesive device according to FIG. 1 with the release liner fully removed.

FIG. 4 also shows the fold 52 on the first release liner 39 of the base layer 22. For clarity's sake, the fold 52 and unattached portion 54 of the second release liner 43 of the base layer 22 are removed. Preferably, the catheter securement bandage 20 includes a fold 52 and an unattached portion 54 on each one of the first and second release liners 39, 43 of the base layer 22. FIG. 7 shows the first and second release liner 39, 43 removed from the base layer 22 exposing the adhesive 38.

The first release liner 39 is shown in FIG. 4 to include a fold 52. Preferably, the total length 74 of the first release liner 39 is longer than the total length 72 of the base layer 22. The second release liner 43 may also be similarly sized as shown in FIG. 5. This allows a medical care giver to pull, on flaps 41, shown in FIG. 5, to remove the first and second release liners 39, 43.

The top layer 24 is also shown in FIG. 5 to include a multi-ply laminate 48. The top layer 24 includes a first layer of adhesive 51 on a top surface 64 of the top layer 24 which is covered by the release liner 67. A second layer of gauze 45 can be coated with the adhesive 38 or impregnated with it. A third layer of plastic 47 on the bottom side 66 of the top layer 24 prevents the second layer of gauze 45 and first layer of adhesive 51 on the top layer 24 from sticking to clothing or other objects. In order to secure a lure connector 30 and hub portion 32 of a catheter 34 in place, as shown in FIGS. 1 and 2, the release liner 67 may be gripped by the flap 41 and removed to expose the adhesive 38 on the top layer 24.

After the release liner 67 is removed, from the top layer 24, best shown in FIGS. 3 and 6, the first adhesive tab 26 and the second adhesive tab 28 may be separated about the perforation 42 and respectively attached to the hub portion 32 and lure connector 30 shown in FIGS. 1 and 2. As discussed above with respect to FIGS. 3 and 6, a central portion 60 on the top surface 58 of the base layer 22 may include adhesive 38. This adhesive 38 helps secure the hub portion 32 and lure connector 30 in place by providing adhesive 38 to fully cover the outer circumference of each with adhesive 38. This is an added advantage over hook and loop devices, which cannot stick to the hub portion 32 and lure connector 30.

Following removal of the release liner 67 on the top layer 24, shown in FIGS. 3 and 6, each one of the first adhesive tab 26 and second adhesive tab 28 may be separated along the perforation 42. As shown in FIG. 2, the first adhesive tab 26 with exposed adhesive 38 may be wrapped around the hub portion 32 to fully surround the circumference. The remaining portion of the first adhesive tab 26 may then be affixed to the top surface 58 of the base layer 22 to retain the hub portion 32 in proper position.

One advantage of wrapping the first adhesive tab 26 around the hub portion 32 is that a central axis 59 of the hub portion 32 may be positioned at an inclined angle 56 relative to the surface of the patient's skin 61. In other words, the hub portion 32 and the catheter 34 are angled relative to the patient's skin 61 to prevent kinking of the catheter 34 due to an extreme bend as it passes through the skin 61. The catheter 34 may then enter the patient's skin at the inclined angle 56 as it is inserted into a blood vessel. Since the first adhesive tab 26 wraps around the hub portion 32, it can be properly elevated and tilted when secured to the top surface 58 of the base layer 22. By including adhesive 38 on the first adhesive tab 26 as well as the central portion 60 of the base layer 22 the hub portion 32 is positively retained in the inclined position. By retaining the hub portion 32 and catheter 34 at an incline, the catheter is less likely to be kinked and obstruct flow. Should the hub portion 32 and catheter 34 be retained horizontally, as is done in the prior art, the catheter 34 enters the patient's skin with a sharp bend when transitioning from the catheter securement bandage 20 into the patient. This kink has been shown to cause restriction or even obstruction of flow through the catheter 34.

As shown in FIG. 2, the top layer 24 preferably attaches to the base layer 22 along the central portion of the base layer. In this part of the top layer 24, there is an adhesive 38 coating both sides of the top layer 24 to retain the top layer 24 connected to the base layer 22 and also provide added adhesive 38 to contact the lure connector 30 and hub portion 32.

As previously mentioned, the central axis 59 of the hub portion 32 may be positioned with an inclined angle 56 relative to a patient's skin by wrapping the first and second adhesive tabs 26, 28 around the circumference of the hub portion 32 and lure connector 30, respectively. This causes the hub portion 32 to tilt and prevent kinking as the catheter 34 enters the skin. The adhesive 38 on the first and second adhesive tabs 26, 28 and the central portion 60 of the top surface 58 of the base layer 22 keeps the lure connector 30 in position after it is attached to the hub portion 32. Pull strength measured by both pulling the catheter 34 and pulling the lumen 36 has shown that due to the third layer of plastic 44 and second layer of gauze 45 in all parts of the catheter securement bandage 20, the hub portion 32 and lure connector 30 are kept at the proper inclined angle 56 despite significant tugging force.

Although the best mode contemplated by the inventors of carrying out the present invention is disclosed above, practice of the present invention is not limited thereto. It will be manifest that various additions, modifications, and rearrangements of the features of the present invention may be made without deviating from the spirit and scope of the underlying inventive concept.

Moreover, the individual components need not be formed in the disclosed shapes or assembled in the disclosed configuration, but could be provided in virtually any shape and assembled in virtually any configuration. Furthermore, all the disclosed features of each disclosed embodiment can be combined with, or substituted for, the disclosed features of every other disclosed embodiment except where such features are mutually exclusive.

It is intended that the appended claims cover all such additions, modifications, and rearrangements. Expedient embodiments of the present invention are differentiated by the appended claims.

We claim:

1. A peripheral intravenous and arterial catheter securement device comprising:
   a base layer formed with a multi-ply laminate comprising a first layer of adhesive, a second layer of gauze, and a third layer of plastic;
   a first release liner protecting at least a portion of the adhesive on the base layer;
   a second release liner protecting at least an additional portion of the adhesive on the base layer;
   a top layer formed with a multi-ply laminate comprising a first layer of adhesive, a second layer of gauze, and a third layer of plastic wherein the first layer of adhesive on the top layer secures to the third layer of plastic on the base layer;
   the top layer comprising:
     first adhesive tab configured to attach to a hub portion of a catheter with an adhesive;
     a second adhesive tab configured to attach to a lure connector with an adhesive; and wherein
   the first adhesive tab and the second adhesive tab each includes a free-floating end not attached to the base layer; and
   a first length of the first and second release liner in contact with the first layer of adhesive on the base layer;
   a free-floating end of the first and second release liner lot in contact with the first layer of adhesive on the base layer and wherein;
   the first release liner and the second release liner only partially contact the first layer of adhesive on the base layer and each include a length greater than a length of the base layer.

2. The peripheral intravenous and arterial catheter securement device of claim 1, wherein the first release liner and the second release liner each comprises an unattached portion not in contact with the first layer of adhesive on the base layer.

3. The peripheral intravenous and arterial catheter securement device of claim 1, further comprising a perforation along a central portion of the top layer effectively equally dividing at least a portion of the top layer into the first adhesive tab and the second adhesive tab.

4. The peripheral intravenous and arterial catheter securement device of claim 3, wherein the top layer further comprises a free-floating end not in contact with the base layer.

5. The peripheral intravenous and arterial catheter securement device of claim 4, wherein the perforation extends only, along the free-floating end of the top layer.

6. The peripheral intravenous and arterial catheter securement device of claim 1, wherein the first adhesive tab secures the huh portion of the catheter at an inclined angle with respect to an entry point in the patient such that a catheter tube attached to the hub portion enters the entry point at the inclined angle.

* * * * *